United States Patent [19]

Monget

[11] 4,308,348
[45] Dec. 29, 1981

[54] TEST FOR BACTERIA

[75] Inventor: Daniel Monget, Lagnieu, France

[73] Assignee: Laboratoire de Recherche API,
Montalieu Vercieu, France

[21] Appl. No.: 147,288

[22] Filed: May 6, 1980

[30] Foreign Application Priority Data

May 25, 1979 [FR] France .................. 79 14355

[51] Int. Cl.$^3$ .............................. C12Q 1/10
[52] U.S. Cl. .................... 435/38; 435/873;
435/879; 435/880; 435/881
[58] Field of Search .............. 435/38, 19, 34, 36,
435/37, 39, 40, 253, 822, 873, 879, 880, 881

[56] References Cited
U.S. PATENT DOCUMENTS 3,832,288 8/1974 Rollender et al. ............ 435/38 X
4,010,078 3/1977 Taylor ........................ 435/38
4,070,247 1/1978 Burt .......................... 435/38

*Primary Examiner*—Robert J. Warden
*Attorney, Agent, or Firm*—Karl F. Ross

[57] ABSTRACT

A test for the detection of bacteria of the genuses Salmonella and Serratia and distinguishing them from the genuses Proteus and Providencia carried out in the presence of a diazonium salt and a synthetic enzymatic substrate in the form of an ester having an aliphatic chain of 7 to 10 carbon atoms. Two reactions may be effected in the same reactive medium. The test may be associated with other tests such as the β-glucosidase, β-galactosidase and β-glucuronidase research tests making it possible to apply it simultaneously to the detection of bacteria belonging to other genuses: Kliebsiella, Enterobacter, Escherichia.

5 Claims, No Drawings

TEST FOR BACTERIA

This invention relates to a test making it possible to show evidence of bacteria of the genus Salmonella and Serratia and distinguish them from the genus Proteus and Providencia.

It is a well known fact that Salmonella are enterobacteria which are responsible for serious infections in man and animals.

They must be sought out in each case of infection, in stools, in particular; they must also be sought out in food products for several of their presence in these products may cause serious infections, and all the more so as sophisticated food products develop (cooked dishes, frozen products) and in large kitchens.

The identification of Salmonella at present requires well known techniques based on indication of their biochemical characteristics. They are thus distinguished from the other enterobacteria and in particular Proteus which are normally present in stools. The method normally followed is to isolate them in a culture medium in order to obtain isolated colonies of each species present: these colonies are then subjected to several biochemical tests, in order to identify them.

The purpose of this invention is to combine, in a single test, two original characteristics selected for their discriminating capacity in respect to enterobacteria.

First of all the test is an enzymatic test indicating an asterase peculiar to the genus Salmonella and Serratia.

Numerous experiments carried out by the applicant on 280 strains of enterobacteria have shown that those belonging to the genus Salmonella and Serratia are practically the only ones capable of hydrolyzing the esters which have an aliphatic chain of 7 to 10 carbon atoms such as 2-naphthylnonanoate, the hydrolysis taking the form of a violet colored complex, in the presence of a diazonium salt and more particularly Fast Blue BB.

The "asterase" test, used to characterise the two Salmonella and Serratia genuses may be effected as follows:

In a microtube containing a quantity of 2-naphthylnonanoate of between 5 and 500 nanomoles, and preferably 20 to 100 nanomoles, $10\mu$ to 1 ml are added of neutralized solution of peptonized water or any other aqueous medium, having a pH close to neutral or slightly alkaline.

A colony of bacteria, isolated from a 24 h culture in a gelose medium, is then placed in suspension in the microtube.

After an incubation period from 5 minutes to 48 h, between 20° C. and 50° C., preferably 2 h to 8 h at 37°, a drop of Fast Blue BB (SIGMA No. F 0250) is added to the concentration at 1 mg to 100 mg/10 ml of $H_2O$, preferably 3 to 10 mg/10 ml. A positive reaction takes the form of the appearance of a violet coloration, making it likely to suspect the presence of bacteria belonging to the genuses Salmonella or Serratia.

It must be noted that the test may be applied not only to a colony in suspension, but also to a suspension obtained from a part of all of a pure culture on a gelose medium, as well as a culture in a liquid broth.

What is more the test may also be carried out directly on a culture in a gelose medium, provided the 2-naphthylnonanoate has previously been incorporated in this medium, at the time it was made. Only the colonies of Salmonella and Serratia are colored violet, on the surface of the gelose, after the addition of Fast Blue BB.

Finally it is perfectly possible to use diazonium salts other than Fast Blue BB, as the detecting agent, for example Fast Blue B, Fast BR, Fast Violet B, etc., and instead of 2-naphthyl-nonanoate, it is also possible to use the 2-naphthyl esters which have an alephatic chain of 7, 8 and 10 carbons (2-naphthylheptanoate, caprylate, caprate).

The esters with 7, 8, 9 and 10 carbons of 1-naphthol or any other replacement naphthol (naphthol AS, etc...) also give results comparable to those of 2-naphthol.

The esters of orthonitrophenol, paranitrophenol, of hydroxycoumarin, of Indoxyl, whether or not substituted, of 4-methyllumbelliferole, of fluorosceine, of phenolphthalsine, of esculatin, of hydroxyquinoline, having an alephatic chain of 7 to 10 carbon atoms also give satisfactory results, for example, after hydrolysis, the nitrophenol substrates spontaneously develop a yellow coloration, the derivatives of indoxyl a blue coloration, while 4-methylumbelliferole emit a 360 nanometres blue fluorescence.

The applicant has also observed that when a diazonium salt is added and more particularly the salt designated under the name Fast Blue BB with a dense suspension of Proteus or Providencia in distilled water, the neutral pale yellow coloring of Fast Blue BB, instead of disappearing gradually under the action of the light as is generally found, intensifies and connot be eliminated, even when the suspension is subjected to the radiation of a camera flashlight.

This phenomenon does not occur with the other genus of bacteria, showing the existence of a compound peculiar to the Proteus and Providencia capable of forming a stable colored complex with Fast Blue BB.

It should be noted that it is possible to reproduce this phenomenon with other salts, such as Fast Violet B, Fast Blue B and Fast Blue BR.

The test may be effected as follows:

A colony of bacteria isolated from a 24 h culture on a gelose medium, is homogenized in a microtube containing 10 $\mu$l to 1 ml of distilled water, of neutralized solution, of peptonised water or any other aqueous medium with a pH close to neutral. After incubation for a period from 5 minutes to 48 hours between 20° C., preferably 2 h to 8 h at 37° C., a drop of Fast Blue BB (SIGMA F 0250) is added to the concentration of 1 mg to 100 mg/10 ml of $H_2O$, preferably 3 to 10 mg/10 ml. If the yellow color of the Fast Blue intensifies and persists even under the action of light, the colony analyzed belongs to the genuses Proteus or Providencia.

It should be noted that although the test concerns a colony in suspension it may also be carried out on a suspension obtained from part of all of a pure culture in a gelose medium, as well as a culture in a liquid broth.

A test may also be carried out directly on a culture in a gelose medium. Only the colonies of Proteus or Providencia on the surface of the gelose will be colored yellow, following the addition of Fast Blue BB.

According to the present invention there is provided a test making it possible to detect bacteria of the genuses Salmonella and Serratis, and distinguish them from the genuses Proteus and Providencia in the presence of a diazonium salt and a synthetic enzymatic substrate in the form of an ester having an alephatic chain of 7 to 10 carbon atoms.

The diazonium salt is preferably Fast Blue BB. The enzymatic substrate should be selected from among the derivatives of the naphthols and especially the 2-naphthylheptanoate, caprylate, nonanote and caprate.

According to another characteristic of the invention the enzymatic substrate may be selected from the esters of orthonitrophenol, paranitrophenol, hydroxy-coumarin, indoxyl, whether or not substituted, 4-methylumbelliferone, fluoresceine, phenolphthaleine, esculetin, hydroxyquinoline, having an alephatic chain of 7 to 10 carbon atoms.

The two reactions should be effected in the same reactive medium.

Preferably the reagents of the test are combined together in a microtube.

The test according to the invention may also be connected with other tests which are already well known such as the tests to seek out -glucosidase, -galactosidase, -glucuronidase which makes it possible at the same time to apply it to the detection of bacteria belonging to other genuses: Klabsiella, enterobacteria, escherichia..

The microtube or microtubes may by advantage be integrated in a device which also includes a gelose medium in order to make it possible to carry out additional tests, such as serological tests, on the basis of the culture which will be developed in the medium.

Research into these characteristics may as an advantage be effected/directly in an isolating medium by including in it the substrates necessary for a reaction.

This invention will moreover be better understood and its advantages will come out more clearly from the examples which follow.

EXAMPLE 1

Characteristics of the genuses Salmonella & Serratia/Proteus & Providencia

To distinguish the Salmonella and Serratia group from the Proteus and Providencia group it is sufficient to use the test in accordance with this invention.

In order to do this, a paper disc is impregnated with 100 nanomoles of 2-naphthylnonanoate. After having deposited the dried disc in the bottom of a microtube, a drop of peptonised water with a pH of 7.5 is then introduced. A colony of bacteria isolated on a gelose medium is taken and homogenized on the surface of the disc. After this operation, the microtube, placed in an incubation box in a damp atmosphere, is incubated for 3 h at 37° C. The presence of esterasic activity peculiar to the genuses Salmonella and Serratia is shown by the appearance of a violet coloration, in the presence of Fast Blue BB SIGMA No. F 0250 with 7 mg/10 ml of $H_2O$. The development of a yellow coloration in the presence of this same Fast Blue, however, characterises the genuses Proteus and Providencia.

An interpretation of the two tests is given in the table below:

| Esterase | + | − |
|---|---|---|
| Proteus & Providencia test | − | + |
| Bacterial genus suspected | Salmonella or Serratia | Proteus or Providencia |

EXAMPLE 2

Characterisation of the genuses Salmonella/Serratia/Proteus & Providencia

The β-glucosidase research, together with the test in example 1, also makes it possible to distinguish Salmonella and Serratia. The substrate used is 4-methylumbelliferyl βD-glucoside, which develops a blue fluorescence at 360 nanometres, when it is hydrolyzed.

In this example, the disc of paper is impregnated with:
100 nM of 2-naphthyl-nonanoate
100 nM of 4-methylumbelliferyl-β-D-glucoside The sequence of the operating method is the same as previously. The -β-glucosidase test is read before the Fast Blue BB is added. An interpretation of the results is given in the table which follows:

| Esterase | + | + | − |
|---|---|---|---|
| Proteus & Providencia test | − | − | + |
| glucosidase | + | − | ± |
| Genus of bacteria suspected | Serratia | Salmonella | Proteus or Providencia |

EXAMPLE 3

Characterisation of the genuses Salmonella/Serratia/Proteus & Providencia/Klebsiella & Enterobacter/Escherichia Coli In order to distinguish the various genuses or groups of genuses, it is sufficient to supplement the test described in Example 2 with β-galactosidase research. The substrate used is paranitrophenyl-β-D-galactoside, hydrolysis of which takes the form of the spontaneous appearance of a yellow coloration.

In this example the disc of paper is impregnated with:
100 nM of 2-naphthylnonanoate
100 nM of 4-methylumbelliferyl-β-D-glucoside
100 nM of paranitrophenyl-β-D-galactoside.

The sequence of the modus operandi is the same as in Example 1.

In the "β-glucosidase" and "β-galactosidase" tests are read before the Fast Blue BB is added.

The table below summarises the interpretation of the results:

| Esterase | + | + | − | − | − |
|---|---|---|---|---|---|
| Proteus & Providencia test | − | − | + | − | − |
| β-glucosidase | + | − | ± | + | − |
| β-galactosidase | ± | −(1) | − | ± | + |
| Genus of bacteria suspected | Serratia | Salmonella | Proteus or Provi. | Kliebsiella & Enterobacter | E. Coli |

(1)The Salmonella arizonae are generally "β-galactosidase" positive

What we claim is:
1. A method for the detection of bacteria of the genuses Salmonella and Serratia and for distinguishing said bacteria from bacteria of the genuses Proteus and Providencia which comprises the steps of:
   (a) wetting a substrate with an aqueous medium having a pH close to neutral wherein said substrate comprises a $C_7$ to $C_{10}$ aliphatic ester of a compound selected from the group consisting of 1-naphthol, 2-naphthol, o-nitrophenol, p-nitrophenol, a hydroxy-coumarin, an indoxyl, a 4-methyl-umbelliferole, fluorescein, phenolphthaleine, esculetin, and a hydroxy-quinoline;

(b) contacting the substrate with a cultured colony of bacteria suspected to belong to the genuses Salmonella and Serratia;

(c) incubating the colony of bacteria;

(d) contacting the colony of bacteria and the substrate with a diazonium salt capable of a color change indicating hydrolysis of the $C_7$ to $C_{10}$ aliphatic ester defined in step (a); and (e) relating any change in color to the presence of either the genuses Salmonella and Serratia or to the genuses Proteus and Providencia.

2. The method defined in claim 1, step (a), wherein the $C_7$ to $C_{10}$ aliphatic ester is selected from the group consisting of 2-naphthyl-heptanoate, 2-naphthyl-caprylate, 2-naphthyl-nonanoate and 2-naphthyl-caprate.

3. The method defined in claim 1, step (d), wherein the diazonium salt is selected from the group consisting of Fast Blue BB, Fast Blue B, Fast Blue BR and Fast Violet B.

4. The method defined in claim 1, further comprising the step of testing for bacteria in addition to those of the genuses Salmonella and Serratia or the genuses Proteus and Providencia.

5. The method defined in claim 1, further comprising the step of distinguishing Salmonella from Serratia.

* * * * *